United States Patent [19]

Brindell et al.

[11] 4,020,113
[45] Apr. 26, 1977

[54] 4,4'-METHYLENEBIS(2,6-DIISOBUTYL-PHENOL)

[75] Inventors: Gordon D. Brindell, Crystal Lake; Rudy F. Macander, Cary, both of Ill.

[73] Assignee: The Quaker Oats Company, Chicago, Ill.

[22] Filed: Jan. 15, 1972

[21] Appl. No.: 253,341

[52] U.S. Cl. .................. 260/619 A; 260/45.95 H
[51] Int. Cl.² .......................................... C07C 39/16
[58] Field of Search ............................ 260/619 A

[56] References Cited

UNITED STATES PATENTS

| | | | |
|---|---|---|---|
| 2,430,002 | 11/1947 | DeGroote et al. | 260/619 A X |
| 3,175,010 | 3/1965 | Coffield et al. | 260/619 A |
| 3,211,652 | 10/1965 | Hinkamp | 260/619 A X |
| 3,227,678 | 1/1966 | Weaver | 260/619 A X |

*Primary Examiner*—Norman Morgenstern
*Attorney, Agent, or Firm*—Joseph P. O'Halloran; Grace J. Fishel

[57] ABSTRACT

A new series of compounds having the following formula is disclosed:

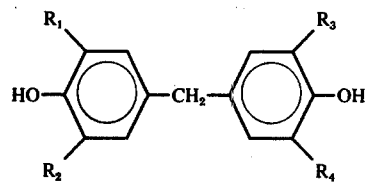

wherein $R_1$, $R_2$, $R_3$, and $R_4$ are alkyl with the proviso that the alkyl groups contain no branching on the carbon alpha to the phenylene group but have at least one branch on the carbon beta to the phenylene group, said compounds useful to stabilize organic materials normally tending to undergo oxidative deterioration.

1 Claim, No Drawings

4,4'-METHYLENEBIS(2,6-DIISOBUTYLPHENOL)

BACKGROUND OF THE INVENTION

1. Field of the Invention

This invention relates to a new class of antioxidants.

2. Description of the Prior Art

In U.S. Pat. No. 3,227,678, the patentee disclosed a class of phenolic compounds having the following formula as stabilizers for polypropylene:

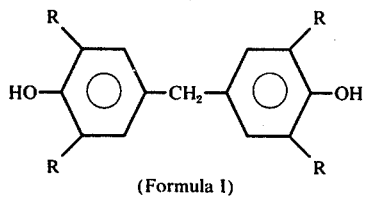

(Formula I)

wherein R is a lower alkyl group having 1 to 6 carbon atoms, which may be primary, secondary, or tertiary. Typical of those compounds were 4,4'-methylenebis(2,6-dimethylphenol), 4,4'-methylenebis(2,6-diisopropylphenol), and 4,4'-methylenebis(2,6-di-tert-butylphenol).

SUMMARY OF THE INVENTION

The purpose of the present invention is to disclose and claim a class of liquid phenolic antioxidants which are unexpectedly good antioxidants for polyolefins.

The present invention may be briefly described as a phenolic compound having the following structural formula:

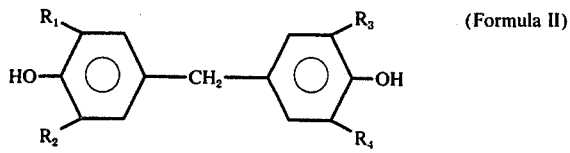

(Formula II)

wherein $R_1$, $R_2$, $R_3$, and $R_4$ are alkyl with the proviso that the alkyl groups contain no branching on the carbon alpha to the phenylene group but have at least one branch on the carbon beta to the phenylene group.

By alkyl in Formula II we mean to include primary alkyl with the further proviso that there is at least one alkyl branch on the carbon atom in said primary alkyl group beta to the phenylene group to which it is attached. We prefer that the alkyl in Formula II contains from 4 to 10 carbon atoms. It is particulary preferred that all the alkyl groups in Formula II, $R_1$, $R_2$, $R_3$, and $R_4$, be primary alkyl groups wherein there is no branching on the carbon atom alpha to the phenylene group but there be one alkyl branch on the beta carbon.

Examples of specific phenolic compounds within the scope of Formula II and useful in the practice of this invention are the following: 4,4'-methylenebis(2,6-diisobutylphenol); 4,4'-methylenebis[2,6-di(2''-methylbutyl)phenol]; 4,4'-methylenebis[2,6-di(2''-methylpentyl)phenol]; 4,4'-methylenebis[2,6-di(2''-ethylpentyl)phenol]; 4,4'-methylenebis[2,6-di(2''-methylhexyl)phenol]; 4,4'-methylenebis[2,6-di(2''-ethylhexyl)phenol]; 4,4'-methylenebis[2,6-di(2''-methyloctyl)phenol]; and 4,4'-methylenebis[2,6-di(-2''-ethyloctyl)phenol].

The phenolic compounds of Formula II are prepared according to methods well known in the art by reacting formaldehyde with a phenol of the following formula:

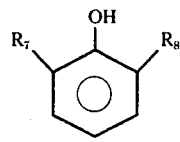

(Formula III)

wherein $R_7$ and $R_8$ are defined consistent with the $R_1$, $R_2$, $R_3$, and $R_4$ groups in Formula II. Exemplary of such methods is that described in U.S. Pat. No. 2,944,086. All of the suitable phenols are commercially available or prepared by known techniques.

The 4,4'-methylenebis(2,6-dialkylphenols) useful as antioxidants for organic materials normally tending to undergo oxidative deterioration. By organic material normally tending to undergo oxidative deterioration, we mean to include material based in whole or in part on a skeleton comprising interconnected carbon atoms which upon exposure to oxygen or air loses its desirable properties and becomes weak, brittle, cracked, discolored, viscous or the like. Exemplary organic materials are polymers, hydrocarbon liquids, particularly gasoline and lubricating or fuel oils, hydrocarbon solids or semi-solids, such as waxes, greases and the like; elastomers, such as natural and synthetic rubber; and feeds or foodstuffs.

Typical polymers include polyolefins, polyurethanes, polyethers, and polyamides. Suitable polyolefins include for example polystyrene, polyvinyl chloride, polyvinyledene chloride, polyvinyl fluoride, polyvinyl butyral, polymethyl acrylate, ethylene vinyl acetate copolymers, and ethylene propylene terpolymers. Suitable polyethers include for example polyformaldehyde and polytetramethylene ether glycol.

Hydrocarbon liquids stabilized by the above described tetraphenolic derivatives include motor lubricating oils, gear and transmission fluids based on hydrocarbon oils, and the like. Fuel oils, such as furnace oils and light kerosene fractions, including gas turbine fuels, are also stabilized by our compositions.

Solid or semi-solid hydrocarbons, such as wax and grease, are also improved by incorporation therein of the tetraphenolic compounds used in this invention.

Such solid polymeric elastomers as natural and synthetic rubber are stabilized against hardening, cracking, and checking with the tetraphenolic derivatives described. Exemplary of natural rubbers is Hevea brasiliensis, while synthetic rubbers include polystyrene-butadiene rubber; polybutadiene; polyisoprene; polyneoprene; polybutyl rubber; polynitrile-butadiene rubbers, polystyrene-chloroprene rubbers; polyacrylate-butadiene rubbers; and polyurethane rubber.

The 4,4'-methylenebis(2,6-dialkylphenols) are also useful to enhance the stability of the natural fats and oils, For example, the following edible oils can be stabilized with our compositions; shortening, lard, butter, coconut oil, cotton seed oil, soybean oil, palm oil, corn oil, peanut oil, sunflower seed oil, safflower oil, olive oil, and the like or mixtures thereof. These oils may have been treated, as by hydrogenation, interesterification, or fractional crystallization, to modify their melting points.

The liquid 4,4'-methylenebis(2,6-dialkylphenols) of Formula II are particularly useful with polymers derived from monoolefins having a terminal double bond. Examples of such alpha polyolefins include but are not limited to the following: polyethylene, polypropylene, poly-4-methylpentene-1, poly-1-butene, poly-3-methylbutene-1, and copolymers thereof.

In general, the phenolic compound of Formula II should be used with organic material in an amount effective and sufficient to stabilize the material. The requisite amount will, of course, depend both on the efficiency of the particular phenolic compound and the nature of the organic material to be stabilized. It has been our experience that from 0.01 percent to 10 percent by weight based on the weight of the organic material is sufficient. Amounts down to as little as 0.0001 percent by weight may be effective in some cases.

It is to be understood that the stabilizing effect of the phenolic compounds is considerably enhanced by conventional synergists such as certain sulfides and polysulfides. The synergist is used in conventional amounts. For example, an amount of synergist from about 0.1 percent to about 1 percent by weight of the organic material to be stabilized is satisfactory but we prefer to use from 0.1 percent to 0.5 percent by weight.

As sulfides there may be mentioned dialkylsulfides, particularly wherein the alkyl groups are long chain such as dodecyl groups since the lower dialkylsulfides are too volatile to be effective, di(substituted)-alkylsulfides particularly esters of bis-carboxyalkyl sulfides such as dilauryl, distearyl, ditridecyl, or dioctadecyl thiodipropionates or thiodibutyrates, dibenzylsulfide such as bis(2-hydroxy-5-methylbenzyl)sulfide and bis(3-tert-butyl-2-hydroxy-5-methoxybenzyl)sulfide, diaryl sulfide, sulfides such as diphenyl sulfide, dicresyl sulfide, 2,2'-dihydroxy-5,5 -dimethyl diphenyl sulfide, diphenyldisulfide, dialkyldithiophosphates such as bis(diisopropyldithiophosphoryl)disulfide, and dialkyldithiophosphatomethylphenols.

It will further be understood that the organic material in addition to containing a stabilizing amount of the phenolic compound and a synergist may contain such other ingredients as other antioxidants, coloring agents, fillers, curing agents, etc.

DESCRIPTION OF THE PREFERRED EMBODIMENTS

The following embodiments of this invention are shown for the purpose of illustrating the invention and demonstrate the best mode for practicing the invention. It will be apparent to those skilled in the art that various changes and modifications may be made therein without departing from the spirit and scope of the invention as it is more precisely defined in the subjoined claims.

EXAMPLE 1

In a reaction vessel equipped with a stirrer, condenser, thermometer, and dropping funnel was placed a solution of 17 g of paraformaldehyde and 278 g of 2,6-di-p-methylbenzylphenol in 500 g of ethanol. To this stirred solution maintained under a nitrogen atmosphere at 40° C. was added sulfuric acid in a dropwise manner until 250 g had been added. The mixture was stirred for 1½ hours, cooled, and the solid filtered off. The product was washed with water, filtered, recrystalized from ethanol, and dried. After drying the product which was 4,4'-methylenebis(2,6-di-p-methylbenzylphenol) was obtained in 83 percent yield and had a melting point of 123°–124° C.

EXAMPLE 2

Using the equipment of Example 1, 105 ml of sulfuric acid was admixed with 210 ml of ethanol. To this stirred solution maintained under a nitrogen atmosphere and at a temperature of 30° C. was added 7 g of paraformaldehyde. At a temperature of about 50° C. a mixture of 105 g of 2,6-dibenzylphenol in 60 ml of ethanol was added to the above stirred solution. The total admixture was maintained under a nitrogen atmosphere at about 45°–50° C. for about an hour. The admixture was cooled and the solid filtered off. The product was washed with water, filtered, and air dried. The dried product was extracted with n-hexane, filtered, and recrystalized from ethanol. The product was 4,4'-methylenebix(2,6-dibenzylphenol) which had a melting point of 100°–102° C.

EXAMPLE 3

Using the equipment of Example 1, 200 ml of sulfuric acid was admixed with 400 ml of ethanol. To this stirred solution maintained under a nitrogen atmosphere at 20°–25° C. was added a mixture of 36 g of paraformaldehyde and 636 g of 2,6-di(2''-ethylhexyl)-phenol. The reaction mixture was maintained under a nitrogen atmosphere at 20°–25° C. overnight. Then the reaction mixture was extracted with 2 liters of n-hexane and 2 liters of water. The water was separated from the n-hexane fraction and the n-hexane fraction washed with 800 ml of water. The water was again separated from the n-hexane fraction and the fraction was dried with MgSO$_4$. The MgSO$_4$ was removed by filtration from the n-hexane fraction and the n-hexane was stripped from the crude product. The unreacted 2,6-di(2''-ethylhexyl)phenol was removed from the crude product by distillation under a reduced pressure of 0.18 mm of Hg at temperatures up to 240° C. The liquid product was 4,4'-methylenebis[2,6-di(2''-ethylhexyl)-phenol].

EXAMPLE 4

The performance of several phenolic compounds as antioxidants for polypropylene was determined in the following tests.

In Test 1 an 80 g sample of Hercules Pro-Fax 6501 polypropylene powder was mixed in a Brabender Plasticorder in which the mixing chamber was heated to about 200° C. The material was mixed for 5 to 10 minutes until the polypropylene had a workable consistency. A sample of the material was then removed and molded into a 5 mil film. The one-inch diameter circles of the film were cut out and put into an oven maintained at 140° C. After 1 hour in the oven, the sample crumbled.

In Test 2, 0.24 g of dilaurylthiodipropionate was mixed with the 80 g of polypropylene powder and a sample tested for heat aging as in Test 1. The sample lasted for 70 hours before it crumbled.

The procedure of Test 1 was repeated in Test 3 except that 0.08 g of 4,4'-methylenebis(2,6-di-tert-butylphenol) was added to the polypropylene powder. A 5 mil film sample tested as in Test 1 lasted for 16 hours before crumbling.

Test 4 was conducted like Test 2 except that 0.08 g of 4,4'-methylenebis(2,6-di-tert-butylphenol) was also incorporated into the polypropylene powder. The sample from this test lasted for 211 hours.

Test 5 was conducted similarly to Test 1 except that 0.08 g of 4,4'-methylenebis[2,6-di(2''-ethylhexyl)phenol] prepared in Example 3 was added to the polypropylene powder. The sample lasted for 16 hours.

In Test 6 the procedures of Test 2 was repeated except that 0.08 g of 4,4'-methylenebis[2,6-di(2''-ethylhexyl)phenol] prepared in Example 3 was also added to the polypropylene powder. The sample in this test lasted for 691 hours.

EXAMPLE 5

4,4'-Methylenebis[2,6-di(2''-ethylhexyl)phenol] from Example 3 and 4,4'-methylenebis(2,6-di-tert-butylphenol) were evaluated in this example as antioxidants for turbine oil. A modification of ASTM D943-IP157 was used. The following modifications were made: 15 inches of electrolylic copper wire No. 14 Brown and Sharpe gage and 15 inches of low-metalloid steel wire No. 16 Washburn and Moen gage were used to wind the mandrel; 150 ml of an unstabilized base oil provided by American Oil Company was used; oil temperature was held at 150° C. during the test; and air was substituted for oxygen.

In Test 7, 0.63 g of 4,4'-methylenebis(2,6-di-tert-butylphenol) was added to the oil. Every 24 hours a 5–10 g sample of oil was removed from the oil tube. The acid number (mg KOH/g sample) of the sample was determined and the time required to reach an acid number of 2.0 was determined. In this test it took 5 days for the acid number to reach 2.0.

Following the above procedure in Test 8 the effectiveness of 4,4'-methylenebis[2,6-di(2''-ethylhexyl)phenol] in place of the 4,4'-methylenebix(2,6-di-tert-butylphenol) was a stablilizer for turbine oil was determined. In this test it took 2 days for the acid number of the oil to reach 2.0.

The above Examples clearly demonstrate the accomplishment of this invention. Examples 1 and 2 are preparations of 4,4'-methylenebis(2,6-diaralkylphenols) useful for comparison with the 4,4'-methylenebis(2,6-dialkylphenol) prepared in Example 3. Example 3 demonstrates the best mode for preparing the liquid 4,4'-methylenebis(2,6-dialkylphenols) of Formula II. The 4,4'-methylenebis(2,6-diaralkylphenols) in Examples 1 and 2 are solids as is the conventional antioxidant 4,4'-methylenebis(2,6-di-tert-butylphenol). Clearly there is an advantage in having a liquid antioxidant for many applications inasmuch as a liquid is more easily distributed in some material to be stabilized.

Other 4,4'-methylenebis(2,6-dialkylphenols) of Formula II were prepared and also found to be liquids at 26° C.

In Example 4 a comparison of Tests 5 with Test 3 clearly demonstrates the unexpected superiority of phenolic compounds of Formula II as antioxidants in polypropylene over the conventional antioxidant 4,4'-methylenebis(2,6-di-tert-butylphenol). This superiority is even better demonstrated by a comparison of Tests 6 with test 4 wherein a conventional synergist is used with the antioxidant. Tests 1–4 inclusive are not embodiments of our invention but were prepared for the purposes of comparison with Tests 5–6 inclusive.

In Example 5 a comparison of Test 7 with Test 8 shows that phenolic compounds of Formula II do not distinguish themselves as antioxidants in turbine oils in comparison with 4,4'-methylenebis(2,6-di-tert-butylphenol). Tests 7 and 8 are not embodiments of our invention but were prepared to compare with the results of Example 4. The excellent ability of phenolic compounds of Formula II to stabilize polypropylene in Example 4 as compared to that of 4,4'-methylbis(2,6-di-tert-butylphenol) is unexpected in view of their lackluster performance in Example 5 in turbine oil.

From the foregoing description we consider it to be clear that the present invention contributes a substantial benefit to the antioxidant art by providing a new and useful antioxidant for organic materials normally tending to undergo oxidative deterioration.

We claim:
1. 4,4'-methylenebis(2,6-diisobutylphenol).

* * * * *